US00PP20830P3

(12) United States Plant Patent
Álamo et al.

(10) Patent No.: US PP20,830 P3
(45) Date of Patent: Mar. 16, 2010

(54) BLUEBERRY PLANT NAMED 'ALTAIR'

(50) Latin Name: ***Vaccinium corymbosum* L.**
Varietal Denomination: cv. Altair

(75) Inventors: Antonio Abad Álamo, Almonte (ES); José Ulf Hayler López, Almonte (ES); Paul M. Lyrene, Micanopy, FL (US)

(73) Assignee: Royal Berries S.L., Almonte (ES)

( * ) Notice: Subject to any disclaimer, the term of this patent is extended or adjusted under 35 U.S.C. 154(b) by 0 days.

(21) Appl. No.: 12/289,016

(22) Filed: Oct. 17, 2008

(65) Prior Publication Data

US 2009/0210979 P1 Aug. 20, 2009

(30) Foreign Application Priority Data

Feb. 14, 2008 (QZ) ..... PBR 2008/0338

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu
(74) *Attorney, Agent, or Firm*—Buchaanan Ingersoll & Rooney PC

(57) ABSTRACT

A new and distinct Blueberry cultivar is provided that is the product of a controlled breeding program followed by selection. The cultivar flowers and forms fruit that ripens over a wide early-to-mid season. The attractive light blue berries exhibit a pleasant sweet flavor and are readily amenable to harvest. Such berries also exhibit a good post-harvest shelf life. The plant is self-fertile, and displays a generally rounded growth habit with attractive evergreen foliage. A low chilling requirement is also exhibited.

4 Drawing Sheets

Botanical/commercial classification: *Vaccinium corymbosum* L./Blueberry Plant.

Varietal denomination: cv. Altair.

SUMMARY OF THE INVENTION

The new Blueberry cultivar of the present invention was the product of controlled artificial pollination carried out in a greenhouse at Greenwood, Fla., U.S.A., wherein two parents were crossed during 1998 which previously had been studied in the hope that they would contribute the desired characteristics. The female parent (i.e., the seed parent) was the unreleased 'FL 90-4' cultivar (non-patented in the United States). The male parent (i.e., pollen parent) was the unreleased 'FL 96-32' cultivar. The parentage of the new cultivar can be summarized as follows:

'FL 90-4'×'FL 96-32'.

The seeds resulting from the pollination were shipped to Almonte, Huelva, Spain, where they sown during approximately 2000, small plants were obtained which were physically and biologically different from each other and selective research of the progeny was carried out. Selective study during the spring of 2003 resulted in the identification of a single plant of the new cultivar. The new plant initially was designated S03-38-04.

It was found that the new Blueberry plant of the present invention displays the following combination of characteristics:

(a) flowers and forms fruit that ripens over a wide early-to-mid season, (b) displays a generally rounded growth habit with attractive evergreen foliage, (c) is self-fertile, (d) displays a low chilling requirement, and (e) forms in abundance attractive light blue substantially round and firm berries that exhibit a pleasant sweet flavor which commonly are readily amenable to harvest and display a good post-harvest shelf life.

The new cultivar well meets the needs of the horticultural industry and can be grown to advantage for the commercial production of blueberries. The substantially round berry shape is well suited for mechanized picking.

The new cultivar of the present invention can be distinguished from all other Blueberry cultivars known to its originators. Each parent plant is unreleased to the public and accordingly is not available to the public for use as a comparative cultivar. When compared to the 'Sharpblue' cultivar (non-patented in the United States), the 'Sharpblue' cultivar is more susceptible to Leaf Rust. When compared to the 'Santa Fe' cultivar (U.S. Plant Pat. No. 10,788), the 'Santa Fe' cultivar displays a substantially longer chill requirement of approximately 600 hours. When compared to the 'Star' cultivar (U.S. Plant Pat. No. 10,675), the 'Star' cultivar commonly displays a more upright and taller growth habit and is less resistant to Botrytis.

The new cultivar has been asexually reproduced by the rooting of softwood cuttings beginning during the summer of 2003 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Altair'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings were approximately four years of age, and were being grown outdoors at Almonte, Huelva, Spain.

DETAILED DESCRIPTION

Figure 1:
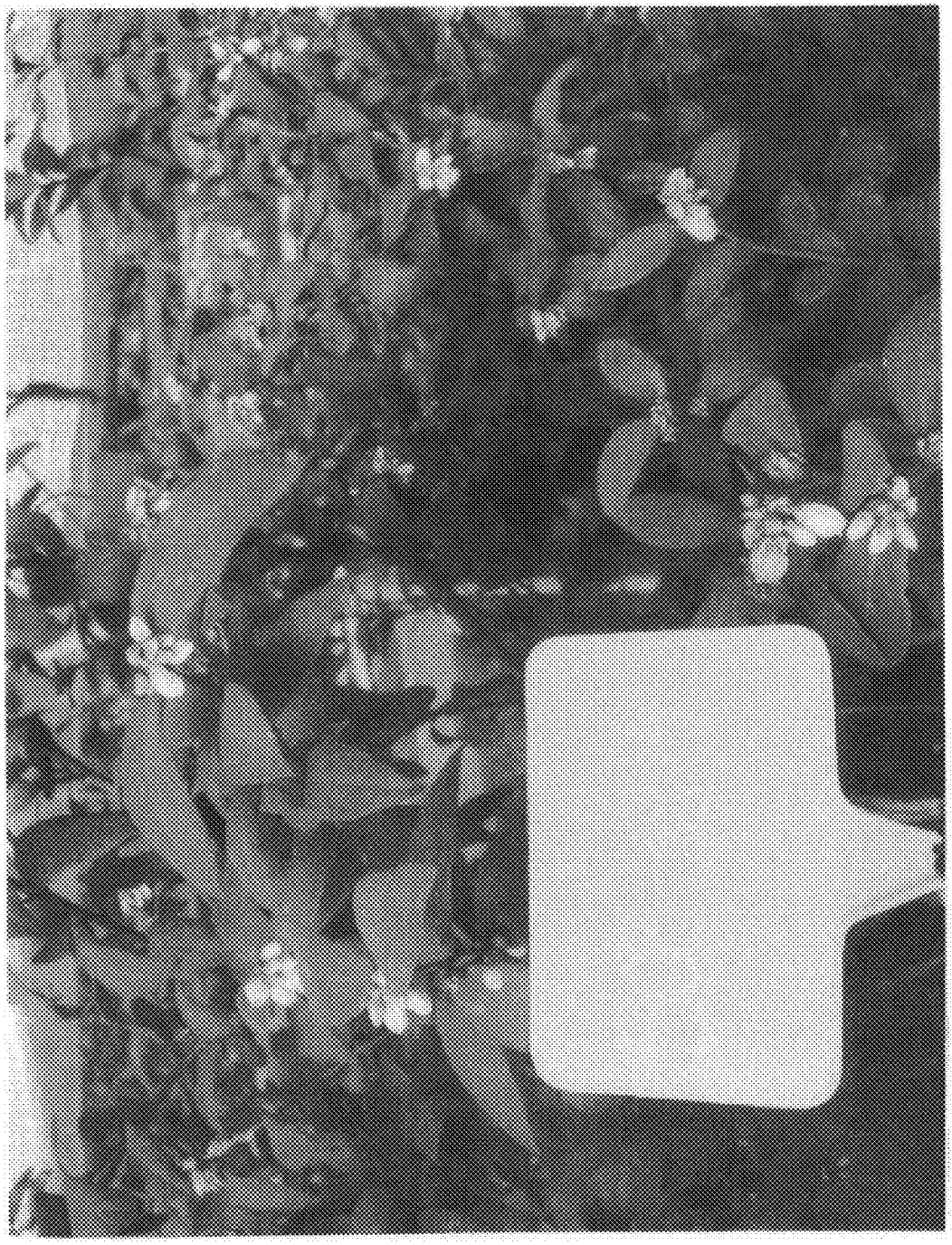
FIG. 1 shows a portion of a typical fruiting plant of the new cultivar while flowering.
Figure 2:
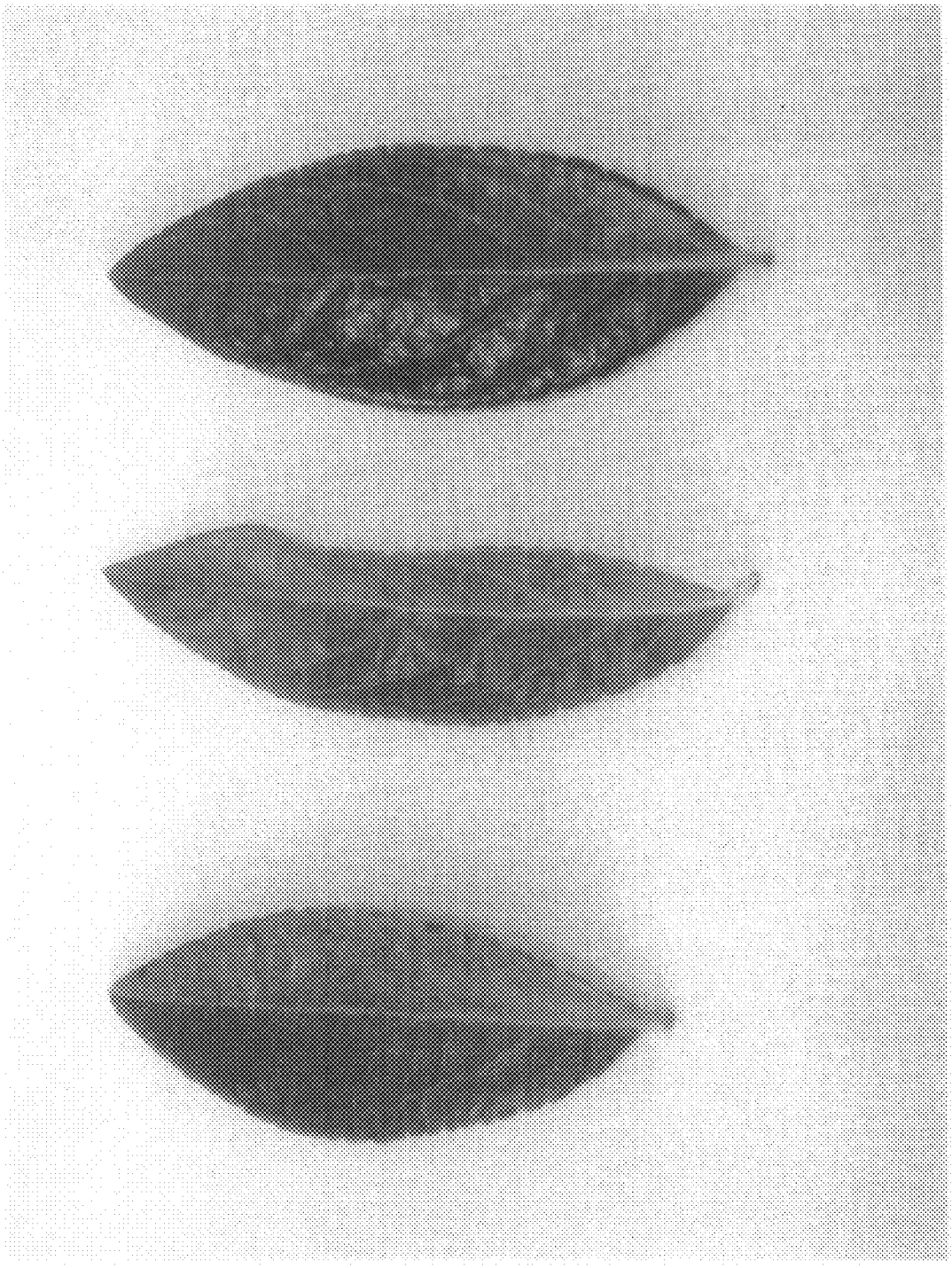
FIG. 2 shows the upper (adaxial) surfaces of typical leaves of the new cultivar.
Figure 3:
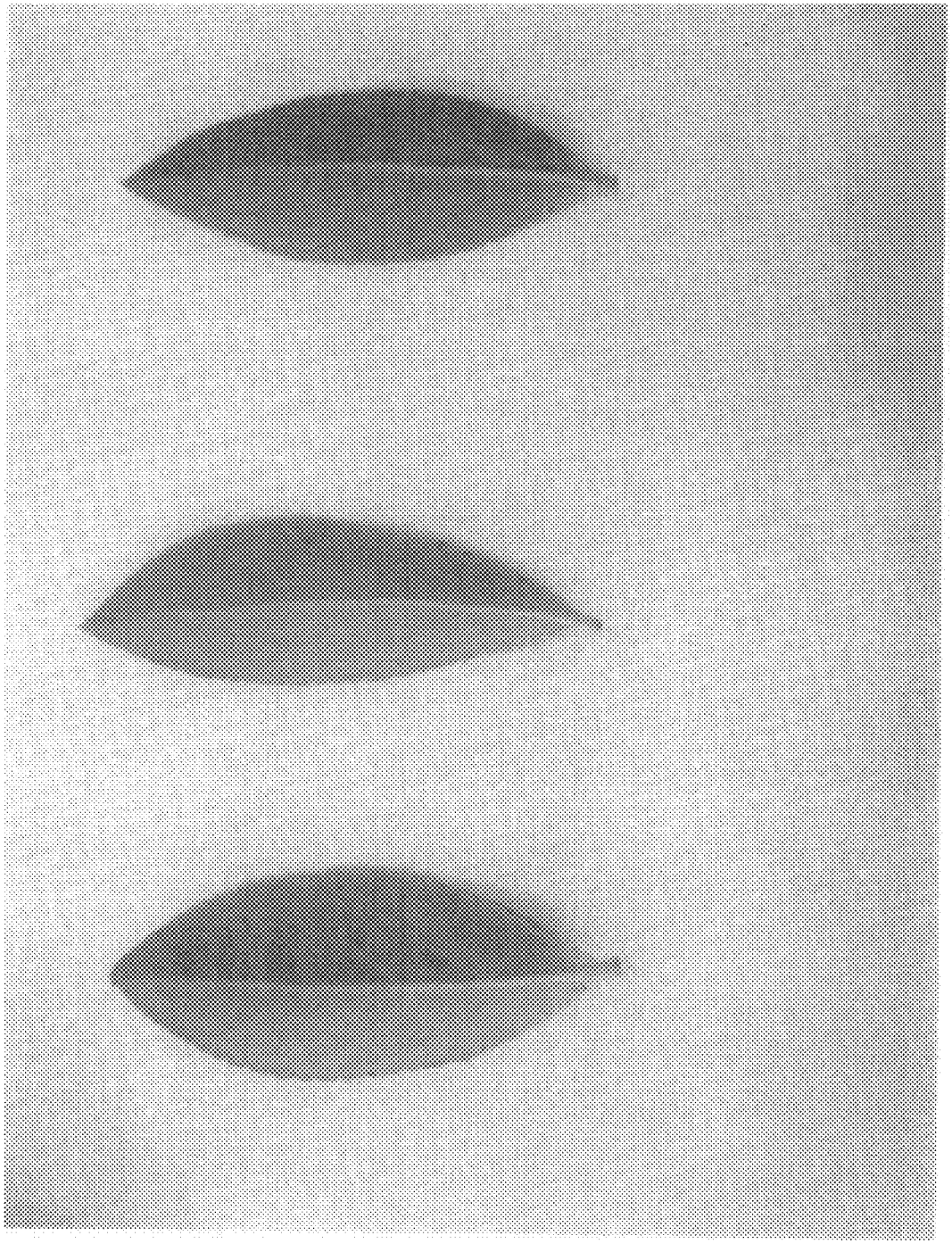
FIG. 3 shows the under (abaxial) surfaces of typical leaves of the new cultivar.
Figure 4:
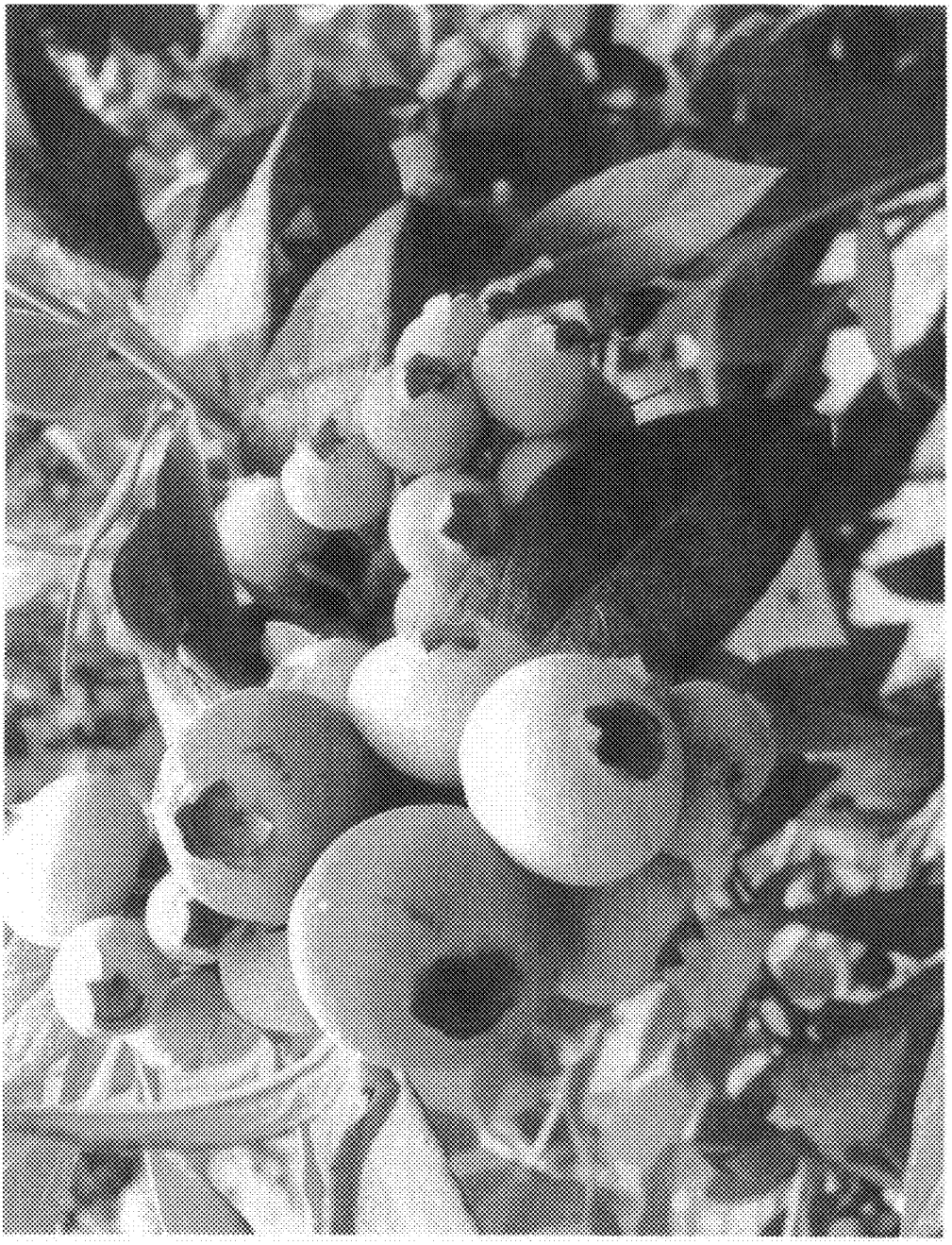
FIG. 4 shows a close view of typical berries of the new cultivar in various stages of development as well as the foliage of the new cultivar.

The chart used in the identification of the colors described herein is The R.H.S. Colour Chart of The Royal Horticultural Society, London, England. Ordinary color terms are to be accorded their customary dictionary significance. The description is based on the observation of approximately four-year-old plants of the new cultivar which had been asexually reproduced by the rooting of cuttings while growing outdoors at Almonte, Huelva, Spain.

Plant:

*Growth habit.*—Generally rounded.

*Height.*—Approximately 1.4 m at 5 years of age.

*Width.*—Approximately 3.7 m at 4 years of age.

*Mature canes.*—Commonly approximately 37.6 cm in length on average, approximately 3 cm in diameter at the base on average, approximately 2.7 cm in diameter towards the tip on average, and near Grey-Brown Group 199D in coloration.

*Foliage retention.*—Evergreen.

*Chill requirement.*—Less than 300 hours.

Foliage:

*Shape.*—Narrowly elliptic.

*Length.*—Commonly approximately 58 mm on average.

*Width.*—Commonly approximately 24 mm on average.

*Apex.*—Acute.

*Base.*—Acute.

*Margin.*—Crenate.

*Texture.*—Glabrous and non-glandular on both surfaces.

*Color.*—Green Group 137A on the upper (adaxial) surface, and Yellow-Green Group 148C on the under (abaxial) surface.

*Petiole.*—Commonly approximately 2.9 mm in length on average, commonly approximately 1.7 mm in diameter on average, near Yellow-Green Group 144D in coloration on the upper surface, and near Yellow-Green Group 145B in coloration on the under surface.

Flowers:

*Time.*—Medium early, at Almonte, Huelva, Spain, with first flower commonly at approximately December $15^{th}$, and 50 percent bloom at approximately February $10^{th}$.

*Number.*—Commonly approximately 7 flowers per inflorescence on average.

*Petals.*—5 in number and fused into a corolla tube.

*Corolla shape.*—Urceolate.

*Corolla size.*—The corolla tube commonly is approximately 10.3 mm in length on average, and approximately 8.8 mm in width on average at the widest point.

*Corolla color.*—Commonly near White Group 155C.

*Calyx.*—Commonly approximately 2.9 mm in length on average.

*Stamen.*—Commonly approximately 10 per flower.

*Filaments.*—Commonly non-adnate, glabrous, pale green in coloration and nearly transparent, and approximately 3.9 mm in length on average.

*Anthers.*—Bronze-colored, and the size ratio of the pollen sac:pollen tube commonly varies from 1:1 to 2:3.

*Pistil.*—One per flower and light green in coloration.

*Style.*—Varies in configuration from cone-shaped to bottle-shaped, approximately 8.5 mm in length on average, and approximately 0.7 to 1 mm in thickness at the base on average.

*Fertility.*—Self-fertile.

*Fragrance.*—None.

Fruit:

*Time.*—Commonly from approximately March 20th to May $30^{th}$ at Almonte, Huelva, Spain (i.e., approximately 10 weeks).

*Shape.*—Substantially round (as illustrated) and firm.

*Height.*—Commonly approximately 17 mm on average.

*Width.*—Commonly approximately 19 mm on average.

*Weight.*—Approximately 2.75 g/berry on average when plants were 4 years of age.

*Fruit scar.*—Approximately 1.4 mm in size and dry.

*Seed number.*—Commonly approximately 25 per berry on average.

*Seed size.*—Commonly approximately 1.2 mm in length on average, and approximately 0.8 mm in width on average.

*Immature color.*—Commonly near Green Group 130D with bloom, and Yellow-Green Group 145B without bloom.

*Mature color.*—Light blue, Violet-Blue Group 97B with bloom, and Black Group 202A without bloom.

*Productivity.*—Abundant, approximately 3.35 Kg/plant on average when plants are 4 years of age.

*Flavor.*—Displays a good sweet flavor.

Development:

*Ability to store.*—The fruit stores well, seven days following harvest when the fruit is stored at 20° C. approximately 96 percent of the berries are good, and seven days following harvest when the fruit is stored at 8° C. approximately 100 percent of the berries are good.

*Disease tolerance.*—No special sensitivity to common Blueberry diseases has been encountered during observations to date at Almonte, Huelva, Spain, and has been shown to be less susceptible to Leaf Rust (*Pucciniastrum vaccinil*) than the 'Sharpblue' cultivar, and more resistant to Botrytis than the 'Star' cultivar.

*Insects.*—Is susceptible to aphids and thrips.

*Cultural conditions.*—Does well in well drained soils and evergreen growing conditions in a low-chilling area with the use of tunnels in an evergreen management system being recommended.

*Heat resistance.*—Has withstood temperatures as high as 45° C. at Almonte, Huelva, Spain.

*Cold resistance.*—Has withstood temperatures as low as −10° C. at Altmonte, Huelva. Spain.

Plants of the 'Altair' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possesses the following combination of characteristics:

(a) flowers and forms fruit that ripens over a wide early-to-mid season, (b) displays a generally rounded growth habit with attractive evergreen foliage, (c) is self-fertile, (d) displays a low chilling requirement, and (e) forms in abundance attractive light blue substantially round and firm berries that exhibit a pleasant sweet flavor which commonly are readily amenable to harvest and display a good post-harvest shelf life;

substantially as herein shown and described.

* * * * *